United States Patent [19]

Kreb, III

[11] 4,065,360

[45] Dec. 27, 1977

[54] CULTURING SYRINGE DEVICE

[76] Inventor: Robert J. Kreb, III, Rolling Road, Skillman, N.J. 08558

[21] Appl. No.: 710,769

[22] Filed: July 30, 1976

Related U.S. Application Data

[63] Continuation-in-part of Ser. No. 678,851, April 21, 1976.

[51] Int. Cl.² .............................................. C12K 1/04
[52] U.S. Cl. ................................ 195/139; 128/2 W; 128/218 M
[58] Field of Search ............... 128/2 W, 272.1, 272.3, 128/218 M, DIG. 5; 195/139, 127

[56] References Cited

U.S. PATENT DOCUMENTS

| 2,541,621 | 2/1951 | Thompson | 128/218 M |
| 3,308,039 | 3/1967 | Nelson | 195/139 |
| 3,734,358 | 5/1973 | Bergeron | 195/139 X |
| 3,848,581 | 11/1974 | Cinqualbre et al. | 128/DIG. 5 |

*Primary Examiner*—Raymond N. Jones
*Assistant Examiner*—Robert J. Warden
*Attorney, Agent, or Firm*—Albert Sperry; Frederick A. Zoda; John J. Kane

[57] ABSTRACT

A syringe device for use with drawing blood or other fluids directly into a sealed sterile environment for culturing which includes a hollow housing defining the syringe chamber therein, further including a movable piston adapted for longitudinal sliding movement within the syringe chamber such that when the piston is withdrawn a partial vacuum is created within the chamber and blood is drawn therein, further including at least one culture cavity defined in the walls of the housing and opening into the chamber within the housing and being adapted to contain therein particularly chosen culturing media in accordance with the particular tests being conducted, further including a sealing means about the periphery of the movable piston such that after the fluid has been drawn into contact with the culturing cavities the piston may be moved back upwardly to seal the culturing media with respect to the outside environment and with respect to the chamber within the syringe to allow for a sterile culturing of the fluid, further including a hollow nipple means adapted to receive a needle detachably affixed thereto to facilitate drawing of fluids into the chamber of the syringe, also including a capping means which is detachably affixable to the nipple means to selectively seal hermetically the chamber from the external environment.

8 Claims, 4 Drawing Figures

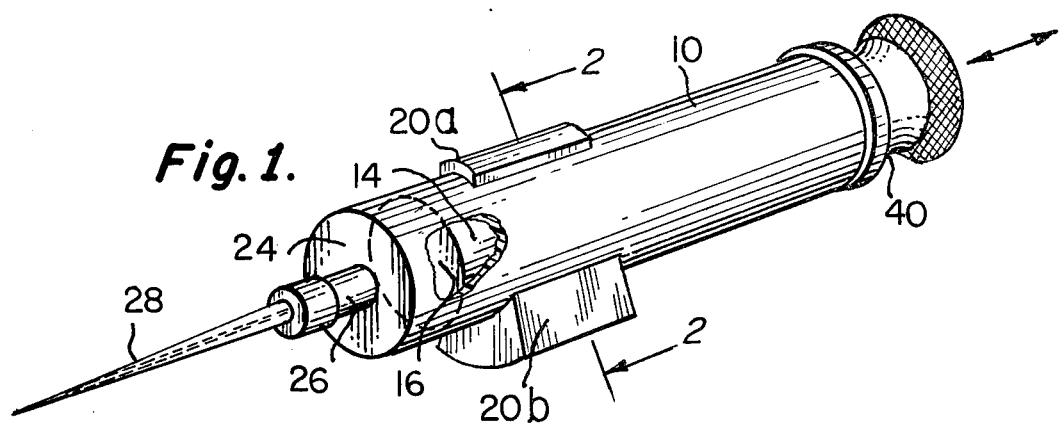
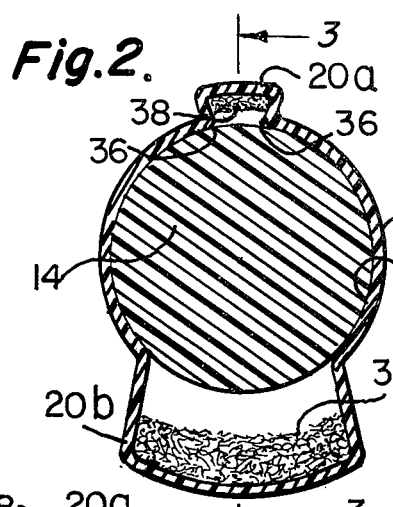
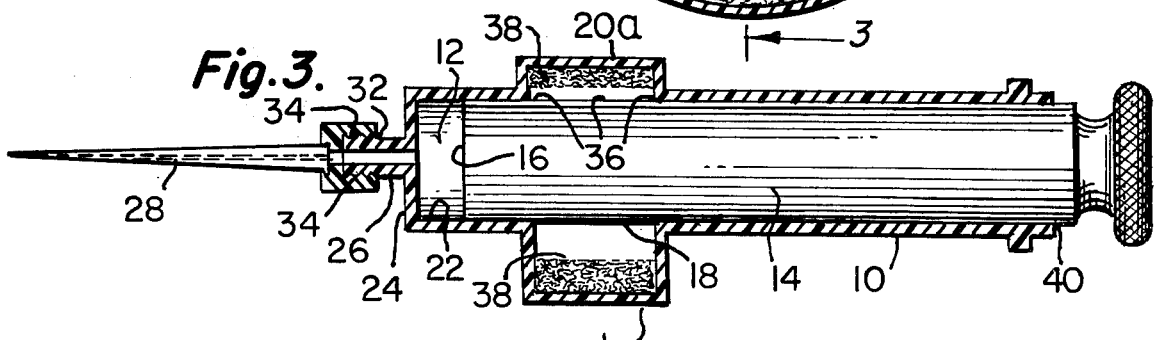
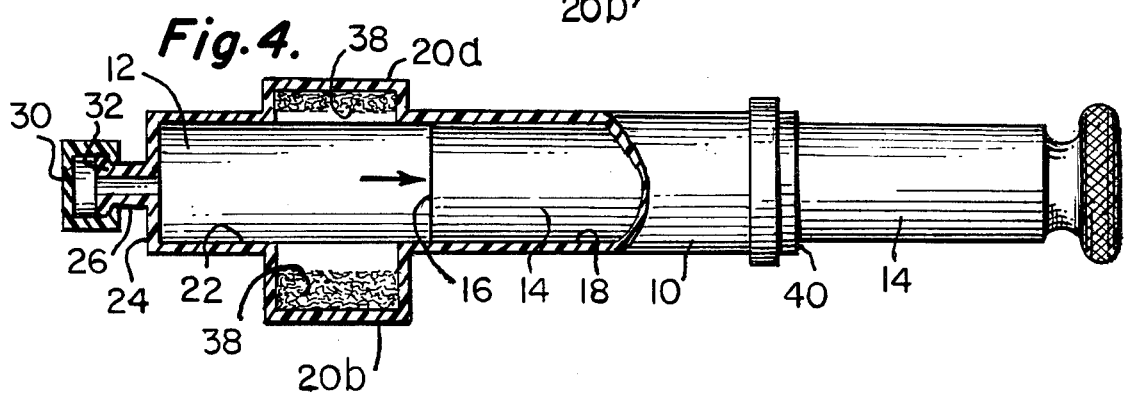

CULTURING SYRINGE DEVICE

This application is a continuation-in-part of pending U.S. Ser. No. 678,851, filed Apr. 21, 1976.

BACKGROUND OF THE INVENTION

1. Field of the Invention

The present invention pertains to the field of culturing devices which are particularly usable in the withdrawing and collecting of blood or other body fluid samplings in order to be placed in a culturing media to test and culture within a completely hermetically sealed culturing media chamber. The present invention provides a testing system which is useful in culturing and transporting the various organisms while maintained within a fully sterile culturing media.

2. Description of the Prior Art

Most culturing systems presently utilized in the prior art are useful in transportation only and does not include the one step fully sterile culturing application of the present invention. When such devices shown in the U.S. Pat. No. 3,783,106 issued to Henshilwood for a testing and culturing transporting system. This system is a good example of the present state of the art in that the sample is withdrawn from the source while exposed to the ambient environment but once it is placed wihin the culturing environment the chamber is sealed to prevent contamination during culturing. However, this Henshilwood system as others in the prior art does not prevent contamination during the movement of the sample to be cultured from the source to the culturing medium environment. Another example of such a patent is U.S. Pat. No. 3,901,219 issued to Kay which utilizes a two step process including the withdrawing of the body fluid by a standard syringe and the replacement of the body fluid within the blood collecting container of the invention at same time thereafter. Difficulties have arisen with this system since contacting of the sample with containers should be minimized to limit the possibility of contamination. Also the system utilizes several steps in order to establish the final sterile environment whereas the present invention achieves the sterile culturing environment in a one step operation.

SUMMARY OF THE INVENTION

The present invention is a culturing syringe device useful for withdrawing body fluids for placing directly into a sterile hermetically culturing environment. The environment is created within a hollow housing which defines a syringe chamber therein. A piston is movably mounted within the hollow housing for longitudinal sliding movement. The piston includes a head area and a peripheral area. The walls of the hollow housing define culturing cavities therein which are filled with culturing media. The peripheral area of the piston is operable to act as a sealing means to hermetically seal the culture cavity after the body fluid is placed therein.

The housing may also include a hollow nipple means in the end of the housing for providing a means for fluid flow communication directly from within the body to the culturing cavities within the chamber. The nipple means includes a mated securing means thereon such as a threaded section or the like which is adapted to receive for mounting upon the nipple means a hollow needle means to aid in withdrawing body fluids and for receiving a capping means to selectively seal the interior of the housing from the external ambient environment. Also defined by the housing is an access opening in the rear portion thereof such that when the piston is withdrawn the access is formed by the diameter of the chamber such to facilitate direct access to the cavities for cleaning or recharging with fresh culturing media.

It is an object of the present invention to provide a device for culturing body fluids in which the fluids are withdrawn and placed into contact with the culturing media and sealed in a one step operation.

It is an object of the present invention to provide a culturing syringe device which is useful for qualitative and quantitative analysis of the bacterial content within a fluid being cultured.

It is an object of the present invention to provide a culturing syringe device which requires two moving parts and permits easy maintenance when utilizing reuseable glass housings.

It is an object of the present invention to provide a device which simultaneously withdraws fluids for culturing from a body and places the fluid in contact with the culturing media and seals the entire system.

It is an object of the present invention to provide a culturing device which can simultaneously place a body fluid in contact with multiple types of culturing media.

It is an object of the present invention to provide a culturing syringe device which includes a multiple means for sealing the culturing media from the external ambient environment.

It is an object of the present invention to provide a disposable culturing syringe device which simultaneously withdraws fluid and places the fluid in contact with the culturing medium.

BRIEF DESCRIPTION OF THE DRAWINGS

While the invention is particularly pointed out and distinctly claimed in the concluding portions herein, a preferred embodiment is set forth in the following detailed description may be best understood when read in connection with the accompanying drawings, in which:

FIG. 1 is a perspective view of an embodiment of the culturing syringe device of the present invention;

FIG. 2 is a cross-section taken through the embodiment of FIG. 1 along lines 2—2;

FIG. 3 is a cross-section of the embodiment shown in FIG. 1 during the withdrawing of body fluids; and FIG. 4 is a cross-section of the embodiment shown in FIG. 1 which is capped and with the piston in the withdrawn position.

DETAILED DESCRIPTION OF THE PREFERRED EMBODIMENT

A preferred embodiment of the culturing syringe device of the present invention includes a housing 10 which may be of a generally tubular configuration as shown in FIG. 1 in order to define therein a generally cylindrical syringe chamber 12. A piston 14 may be movably mounted in the syringe chamber 12 which includes a head area 16 and a peripheral area 18. The peripheral area is in contact with the side walls or lateral housing walls 22. The head area 16 of the piston 14 will contact the end housing wall 24 when the piston is in the completely collapsed position.

Along the lateral housing walls 22 of the housing 10 will be defined one or more culturing cavities 20. These culturing cavities include a culturing medium 38 therein. The various culturing cavities may have similar culturing media or different media depending upon the particular tests to which the culturing syringe device is being applied. The peripheral areas 18 are designed to act as a sealing means 36 whenever the piston is in the collapsed position as shown in FIG. 3 in order to seal each of the culturing cavities 20 with respect to the interior of the syringe chamber 12 and respect to the exterior ambient environment. To selectively communicate or seal the chamber from the external environment the nipple means 26 may be positioned to be defined within the head area 16 of the housing 10. The nipple means 26 includes a mated securing means 32 thereon such as threaded sections 34 which is adapted to secure to a hollow threaded needle means 28 or a capping means 30. Whenever it is desired to withdraw fluids into the chamber through the nipple means 26 the needle means 28 may be affixed thereon to facilitate the withdrawing of body fluids directly from the human body to be placed in contact with the culturing media 38.

The culturing syringe device may be reusable or may be disposable. With reusable systems the housing may be made of a hard glass material to facilitate multiple usage. With such reusable systems it would be desirable to clean the interior of the syringe chamber 12 after each usage and to recharge the culture cavities 20 by placement of culturing media therein. Also the choice of the particular culturing medium 38 being utilized can be changed between usuages.

The cooperation between the peripheral areas 18 of the piston and the lateral housing walls 22 which define the cultured cavities 20 creates a sealing means 36 therebetween to provide a first means of sealing the culturing cavities with respect to contamination. The second means of sealing the culturing media hermetically with respect to contamination is achieved through the use of a capping means such as a cap 30 which may be secured by clip-on or threading upon the nipple means 26. In this manner a second means of sealing will be created to further minimize the chances of contamination within the cultuing environment existant within culturing medium 38.

It should be appreciated that the walls of the cultured cavities 20 can be formed from the same material as the housing 10 or alternative configurations such as removable bags of soft material and the like can be used to facilitate replacement of fresh culturing media 38. Again any configuration rather than the cylindrical sector shown in the Figures of this embodiment may be utilized.

It should be appreciated that the present apparatus has a main functional advantage in the one step operation which simultaneously withdraws fluid from the body and places the fluid in contact with the culturing medium. Also the dual sealing achieved between the culturing environment and the external ambient environment is an advantageous structure which minimizes contamination. Also refreshing of the culturing medium 38 within the various cavities 20 is facilitated by the removal of the piston 14 from within the housing 10.

The present apparatus also facilitates examination of the culturing media for both qualitative and quantitative analysis in that the culturing media can be viewed whenever the material of the housing is translucent. In particular with a glass housing the syringe device itself may be examined under microscope to determine color changes for qualitative analysis of bacterial growth or for counting of bacterial colonies for quantitative analysis.

While particular embodiments of this invention have been shown in the drawings and described above, it will be apparent that many changes may be made in the form, arrangement in positioning of various elements of the combination. In consideration thereof it should be understood that the preferred embodiments of this invention disclosed herein are intended to be illustrative only and not intented to limit the scope of the invention.

I claim:

1. A culturing syringe device for withdrawing the fluid to be cultured directly into a sterile sealed culturing environment comprising:
   a. a hollow housing defining a syringe chamber therein;
   b. at least one closed culturing cavity defined in the lateral walls of said housing to be selectively openable into said syringe chamber, each said closed cavity having culturing media therein;
   c. a movable piston located within the syringe chamber and adapted for longitudinal sliding movement therein, said piston including a head area and a peripheral area, said peripheral area providing a sealing means to selectively seal hermetically said closed culturing cavities from said syringe chamber and from the ambient environment;
   d. hollow nipple means in one end of said housing providing fluid flow communication between said housing and the external environment; and
   e. hollow needle means detachably affixed to said nipple means to allow fluid flow communication with the external environment.

2. The device as defined in claim 1 further comprising a capping means being detachably affixable to said nipple means to selectively seal hermetically said chamber from the external ambient environment.

3. The device as defined in claim 1 further including a mated securing means configured on the exterior of said nipple means and on said needle means.

4. The device as defined in claim 3 wherein said securing means comprises threaded sections.

5. The device as defined in claim 1 wherein said housing is tubular.

6. The device as defined in claim 1 wherein said housing is configured as a hollow cylindrical tube.

7. The device as defined in claim 1 including means for removing said piston from said chamber to allow direct access to said cavities for cleaning and the like including recharging with fresh culturing media.

8. A culturing syringe device for withdrawing fluid to be cultured directly into a sterile sealed culturing environment comprising:
   a. a hollow round tubular housing defining a cylindrical syringe chamber therin;
   b. at least one closed culturing cavity defined in the lateral walls of said housing to be selectively openable internally into said syringe chamber, each said culturing cavity having culturing media therein;
   c. a movable cylindrical piston located within said syringe chamber and adapted for longitudinal sliding movement therein, said piston including a head area and a peripheral area, said piston being removable to facilitate access to the interior of said housing, said peripheral area providing a sealing means to selectively seal hermetically said culturing cavities from said syringe chamber and from the ambient external environment;
   d. hollow nipple means in one end of said housing selectively providing fluid flow communication between said chamber and the external environment;
   e. hollow needle means adapted to be detachably affixed to said nipple means to allow fluid flow communication with the external environment; and
   f. capping means detachably affixable to said nipple means to selectively seal hermetically said chamber from the external environment.

* * * * *